(12) United States Patent
Scancarella et al.

(10) Patent No.: US 6,967,024 B2
(45) Date of Patent: Nov. 22, 2005

(54) LONG WEARING COMPOSITION FOR MAKING UP EYES, SKIN, AND LIPS

(75) Inventors: Neil D. Scancarella, Wyckoff, NJ (US); Jean Marie Manelski, Spring Lake, NJ (US); Julio Gans Russ, Westfield, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 10/703,249

(22) Filed: Nov. 10, 2003

(65) Prior Publication Data

US 2004/0096407 A1 May 20, 2004

Related U.S. Application Data

(63) Continuation of application No. 09/860,749, filed on May 18, 2001, now Pat. No. 6,726,900.

(51) Int. Cl.$^7$ .............................. A61K 7/04; A61K 7/06
(52) U.S. Cl. ........................ 424/401; 424/64; 424/70.7; 424/70.12
(58) Field of Search ...................... 424/64, 70.7, 70.12, 424/401

(56) References Cited

U.S. PATENT DOCUMENTS

| | | | |
|---|---|---|---|
| 2,676,182 A | 4/1954 | Daudt ...................... 260/448.2 |
| 3,541,205 A | 11/1970 | Hardigan ...................... 424/60 |
| 3,836,647 A | 9/1974 | Lange ........................ 424/184 |
| 4,828,826 A | 5/1989 | Franz ........................... 424/63 |
| 5,246,780 A | 9/1993 | Farer ........................... 428/404 |
| 5,324,506 A | 6/1994 | Calvo ........................... 424/63 |
| 5,460,804 A | 10/1995 | Krzysik ....................... 424/60 |
| 5,480,632 A | 1/1996 | Orr ............................... 424/63 |
| 5,512,272 A | 4/1996 | Krzysik ....................... 424/59 |
| 5,599,547 A | 2/1997 | Bartholomey ............... 424/401 |
| 5,609,852 A | 3/1997 | Galley .......................... 424/59 |
| 5,622,694 A | 4/1997 | Torgerson ............. 424/70.122 |
| 5,674,478 A * | 10/1997 | Dodd et al. ................ 424/70.1 |
| 5,725,845 A | 3/1998 | Krog ............................ 424/64 |
| 5,800,816 A | 9/1998 | Brieva .......................... 424/63 |
| 5,837,223 A | 11/1998 | Barone ......................... 424/64 |
| 5,849,275 A | 12/1998 | Calello ......................... 424/64 |
| 5,851,517 A | 12/1998 | Mougin .................... 424/78.02 |
| 5,874,072 A | 2/1999 | Alwattari .................... 424/70.7 |
| 5,916,547 A | 6/1999 | Torgerson ................ 424/70.12 |
| 5,919,439 A | 7/1999 | Torgerson ............. 424/70.122 |
| 5,932,197 A | 8/1999 | Arnaud ......................... 424/64 |
| 5,945,095 A | 8/1999 | Mougin .................... 424/78.02 |
| 5,948,393 A | 9/1999 | Tomomasa ................... 424/63 |
| 5,985,258 A | 11/1999 | Alwattari ................... 424/70.7 |
| 6,019,962 A | 2/2000 | Rabe ............................ 424/64 |
| 6,024,946 A | 2/2000 | Dubief ....................... 424/70.1 |
| 6,071,503 A | 6/2000 | Drechsler .................... 424/64 |
| 6,074,654 A | 6/2000 | Drechsler .................. 424/401 |
| 6,083,516 A | 7/2000 | Curtis ........................ 424/401 |
| 6,126,929 A | 10/2000 | Mougin ..................... 424/70.7 |
| 6,139,823 A | 10/2000 | Drechsler .................... 424/64 |
| 6,159,486 A | 12/2000 | Terren ........................ 424/401 |
| 6,180,123 B1 | 1/2001 | Mondet ...................... 424/401 |
| 6,214,329 B1 | 4/2001 | Brieva ....................... 424/70.7 |
| 6,235,293 B1 | 5/2001 | De La Poterie ............. 424/401 |
| 6,340,466 B1 | 1/2002 | Drechsler .................. 424/401 |
| 6,342,209 B1 | 1/2002 | Patil ............................. 424/61 |
| 6,444,212 B1 * | 9/2002 | Cavazzuti et al. .......... 424/401 |
| 6,620,417 B1 | 9/2003 | Jose ........................... 424/401 |
| 6,726,900 B2 * | 4/2004 | Scancarella et al. .......... 424/64 |
| 2001/0055600 A1 | 12/2001 | Shah .......................... 424/401 |
| 2002/0114773 A1 | 8/2002 | Kanji ....................... 424/70.21 |

FOREIGN PATENT DOCUMENTS

| | | |
|---|---|---|
| JP | 61-158913 | 7/1986 |
| JP | 86-161211 | 7/1986 |
| JP | 5-65212 | 3/1993 |
| JP | 6-24933 | 2/1994 |
| WO | WO 93/17660 | 9/1993 |
| WO | WO 00/47168 | 8/2000 |

OTHER PUBLICATIONS

Phoenix Chemical, Inc., Giovarez AC–5099M, Jan. 1, 1999.
CA Selects: Cosmetic Chemicals, Issue 16, 1997. 127:39527t. Makeup Cosmetics Containing Organosilicones and Volatile Oily Components. May 13, 1997.
CA Selects: Cosmetic Chemicals, Issue 16, 1997. 127:39531q Water in Oil Type Mascaras Containing Organosilicone Resins. May 13, 1997.

* cited by examiner

*Primary Examiner*—Thurman K. Page
*Assistant Examiner*—Sharon Howard
(74) *Attorney, Agent, or Firm*—Julie Blackburn

(57) ABSTRACT

A composition for making up the eyes and skin comprised of a liquid carrier containing at least one film forming polymer, and dispersed therein at least one organic pigment forming the main color component of the composition as well as a method for improving the wear of cosmetic compositions for making up eyes and skin comprising formulating said products with one or more organic pigments in an amount sufficient to improve the wear of the cosmetic composition.

21 Claims, No Drawings

LONG WEARING COMPOSITION FOR MAKING UP EYES, SKIN, AND LIPS

This application is a continuation of U.S. patent application Ser. No. 09/860,749, filed May 18, 2001, now U.S. Pat. No. 6,726,900.

TECHNICAL FIELD

The invention is in the field of compositions for application to eyebrows and eyelashes to impart color, or for use in lining the eyes with color, or application to the skin as in a facial or body tattoo, or the lips as a semi-permanent lipcolor.

BACKGROUND OF THE INVENTION

Many women use a variety of products to beautify the eyes, including brow color, eyeshadow, mascara, and eyeliner. Such products accentuate the eyes and in the case of lash products, will also give the appearance of longer lashes.

One of the common problems with eye products such as liners and mascara is that they often do not wear for long periods of time and have a tendency to smudge. With respect to eyeliner, more adventurous consumers have addressed this problem by having "permanent" eyeliner essentially tattooed onto the eyelids. This is a permanent cosmetic procedure and the eyeliner is not removable.

Cosmetic manufacturers are constantly exploring new formulas for such products that will fill the need gaps of longer wear and reduced smudging in a way that will not necessitate visits to beauty salons to have permanent cosmetics tattooed into the skin. The desired cosmetics should provide long lasting, durable wear, preferably one or more days, and be removable by the consumer whenever desired. In addition, the color should be rich and as natural looking as possible.

Typically, products for making up the eyes contain inorganic iron oxide pigments in an emulsion. Iron oxides are water insoluble and are generally ground with one or more oils in the composition to form what is referred to as a pigment grind. For example, traditional mascaras are mixtures of waxes, oils, and inorganic pigments. They may be anhydrous or in the emulsion form. Many of the so-called water resistant mascaras are anhydrous while traditional mascaras are often in the emulsion form. These types of mascaras are generally applied to the lashes and wear for periods of time ranging from several hours to one day. Users usually remove what remains of such products at the end of the day by washing with water. Another problem associated with such mascaras is their tendency to smudge when the user becomes warm or wears eye makeup that is oily. Moreover, since such products contain significant levels of wax and oil, the inorganic pigments that provide color may tend to be muted. This in turn provides a more artificial look to mascara coated lashes.

Similarly, eyeliner is usually a liquid product or in a pencil form. It is applied to the upper and lower lids to accentuate the eye area. While eyeliner is a very desirable beauty product, it tends to smudge very readily, especially when worn on lower lashes. The smudging is due, in part, to the solubilizing of the dried eyeliner formula by skin oils, perspiration, and tears. Again, the iron oxides typically used to provide color to such products are muted and matte in tone, sometimes providing an artificial look to the liner especially when the color is very dark.

The major need gaps in the field of lash, brow, and liner products relates to creating a color that has a rich, deep, natural tone, and at the same time providing a product that has the capability of extended wear (one or more days) if desired by the consumer, and where negative tendencies such as smudging upon exposure to perspiration, tears, and environmental assaults are reduced or eliminated.

Organic pigments are well known for use in cosmetic compositions. They are particularly desirable because the colors provide a very rich intensity that is not found with traditional inorganic pigments. However, because most organic colors are water soluble, it is difficult to incorporate them into long wearing cosmetics because if the cosmetic user comes into contact with the water such as perspiration, raindrops, etc. the organic pigments readily dissolve in the water and tend to run on the skin and hair. Further, organic pigments are generally not compatible in non-aqueous systems at any appreciable concentration, so they cannot be used in amounts large enough to impart significant color to the composition.

The object of the invention is to prepare products for making up the eyes and skin, such as mascara compositions (or lash tints), brow color, eyeliner, facial or body tattoos that exhibit extended wear, look natural, provide a rich color, and exhibit reduced smudging.

Another object of the invention is to provide eye or face products that are capable of wearing for one to five days and provide a natural appearance.

Another object of the invention is to provide commercially acceptable, stable, products for making up the eyes where the color is obtained with the use of organic pigments.

Another object of the invention is to provide a method for improving the wear of eye or face (the term "face" including lips) product using organic pigments in an amount sufficient to improve wear.

SUMMARY OF THE INVENTION

The invention comprises a composition for making up the eyes and skin comprising a liquid carrier containing at least one film forming polymer, and dispersed therein at least one, preferably a mixture, of organic pigments forming the main color component of the composition.

The invention further comprises a method for improving the wear of cosmetic compositions for making up eyes and skin comprising formulating said products with one or more organic pigments in an amount sufficient to improve the wear of the cosmetic composition.

Preferably the composition exists in a single phase, rather than in emulsion (water-in-oil or oil-in-water) form. The term "single phase" means that the composition exists in one homogeneous phase (such as an oil phase) and the organic pigments used in the composition are dispersed in that phase and the film forming polymer is solubilized in that phase. The term "single phase" also means that one or more of the film forming polymers and the organic pigments may be dispersed in the liquid vehicle and both are compatible and stable therein. In the latter situation, while the film forming polymer may not be completely soluble in the liquid vehicle, it is capable of dispersing in sufficiently small particles throughout the liquid vehicle, remaining dispersed therein in a stable manner, and compatible therewith. In either case, when the composition is applied to the desired surface, the liquid carrier evaporates at least in part and the film forming polymer sets on the surface trapping the pigment particles that were dispersed in that phase on the surface. Preferably, the composition of the invention has a viscosity ranging from 1000 to 500,000, more preferably 5000 to 250,000, most preferably 7000 to 120,000 centipoise at 25° C. The organic pigments used in the claimed compositions comprise the main color component of the composition. The term "main color component" means that the organic pigments are present in an amount sufficient to provide color to the composition, meaning that if the amount of organic pigment which is present is removed the color of the composition will be different when a sample of that composition is drawn across the back of the hand, for example, and visually observed with the naked eye. Preferably, the organic pigments provide at least about 0.1–95%, preferably at least about 45–80%, most preferably at least about 80–90% of the color of the claimed composition. In the most preferred embodiment, the organic pigments provide about 100% of the color of the claimed composition (meaning that when the entire pigment concentration is measured, the percentage of organic pigments in the entire pigment load is reflected in the percentage mentioned). It is possible that the claimed compositions may contain one or more inorganic pigments including but not limited to metal oxides such as titanium, iron, oxides such as black, red, yellow, green, and blue, and similar organic powders.

The compositions of the invention may be in the liquid, solid, or semi-solid form. Preferably, the compositions are liquids or semi-solids.

I. Pigments and Particulate Fillers

A. Organic Pigments

The composition of the invention preferably comprises about 0.05–30%, preferably about 0.1–25%, more preferably about 0.5–20% by weight of the total composition of one or more organic pigments or salts thereof. The organic pigments should be dispersible in the liquid carrier. Particularly preferred are organic pigments that are red, green, blue, yellow, violet, orange, and mixtures thereof. Also suitable are Lakes of such pigments, which means that the organic pigments are reacted with a metal salt such as calcium, aluminum, barium, zirconium, and the like to form salts. Particularly preferred are aluminum Lakes of the organic pigments, which is where the organic pigment is reacted with aluminum to form the aluminum salt. Formation of the metal salt of the organic pigment will generally convert the pigment from a water soluble pigment into a water insoluble pigment. Examples of organic pigment families that may be used herein include azo, (including monoazo and diazo), fluoran, xanthene, indigoid, triphenylmethane, anthroquinone, pyrene, pyrazole, quinoline, quinoline, or metallic salts thereof Preferred are D&C colors, FD&C colors, or Lakes of D&C or FD&C colors. The term "D&C" means drug and cosmetic colors that are approved for use in drugs and cosmetics by the FDA. The term "FD&C" means food, drug, and cosmetic colors which are approved for use in foods, drugs, and cosmetics by the FDA. Certified D&C and FD&C colors are listed in 21 CFR 74.101 et seq. and include the FD&C colors Blue 1, Blue 2, Green 3, Orange B, Citrus Red 2, Red 3, Red 4, Red 40, Yellow 5, Yellow 6, Blue 1, Blue 2; Orange B, Citrus Red 2; and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on. Suitable Lakes of D&C and FD&C colors are defined in 21 CFR 82.51. Particularly preferred are Lakes formed by the reaction of the organic pigment with a metallic salt such as aluminum, calcium, zirconium, barium, and the like. Suitable reds include pigments from the monoazo, disazo, fluoran, xanthene, or indigoid families or Lakes thereof, such as Red 4, 6, 7, 17, 21, 22, 27, 28, 30, 31, 33, 34, 36, and Red 40. Also suitable are Lakes of such red pigments. Typically the metal salts are aluminum, barium, and the like. Most preferred are Aluminum Lakes of the various red pigments mentioned herein.

Suitable yellows include wherein the yellow pigment is a pyrazole, monoazo, fluoran, xanthene, quinoline, or salt thereof Suitable yellows include Yellow 5, 6, 7, 8, 10, and 11, as well as Lakes of such yellow pigments.

Suitable violets include those from the anthroquinone family, such as Violet 2 and Lakes thereof Examples of orange pigments are Orange 4, 5, 10, 11, or Lakes thereof.

The organic pigments form the main color component of the invention meaning that the color of the composition is attributable to the organic pigments. While inorganic oxides may be incorporated into the composition, the main color of the lash tint (which is black or brown) is due to the organic pigment. In the preferred embodiment of the invention the lash tint is a rich dark brown or black in color, which is achieved through the use of a combination of organic pigments which are not black or brown in color. The rich deep brown or black color may be achieved by combining organic pigments or Lakes thereof in the red, green, yellow, blue, violet, and orange family. Preferably the lash tint comprises a mixture of red, green, yellow, and blue organic pigments or Lakes thereof and is deep brown or black in color. In the most preferred composition the pigments comprise a mixture of red, green, yellow, and blue organic pigments wherein the pigments are Lakes, namely they are in the form of water insoluble aluminum salts. These preferred compositions may comprise organic pigments in non-Lake form however, since such pigments are water soluble, when used in large amounts such non-Lake organic pigments may be incompatible with the liquid carrier. If non-Lake organic pigments are present, they are generally present at about 0.0001–3%, preferably about 0.0005–1% by weight of the total composition at most. The most preferred compositions of the invention are dark brown or black in color and are free of iron oxides, particularly black iron oxide, or contain such iron oxides in amounts less than about 5–10% by weight.

B. Inorganic Pigments

In the event the claimed composition contains inorganic pigments, preferred is where the amount is sufficient to accentuate the color achieved with the organic pigment but not obscure the intensity of the organic pigments. Preferred ranges include about 0.001–15%, preferably about 0.005–10%, more preferably about 0.01–8% by weight of the total composition. Suitable inorganic pigments include iron oxides such as red, blue, black, green, and yellow; titanium dioxide, bismuth oxychloride, and the like. Preferred are iron oxides.

C. Particulate Fillers

It may also be desirable to include one or more particulate fillers in the claimed composition. If so, suggested ranges are about 0.001–40%, preferably about 0.05–35%, more preferably about 0.1–30% by weight of the total composition. Preferably, the particulate matter has a particle size of 0.02 to 100, preferably 0.5 to 100, microns. Suitable particle fillers include titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silk powder, silica, talc, mica, zinc laurate, zinc myristate, zinc rosinate, alumina, attapulgite, calcium carbonate, calcium silicate, dextran, kaolin, nylon, silica silylate, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

II. Liquid Carrier

The composition comprises about 0.1–85%, preferably about 5–80%, more preferably about 10–75% by weight of the total composition of a liquid carrier for the film forming polymer and the organic pigments, which may comprise one or more oils or other liquid materials. Preferably the liquid carrier is anhydrous. The term "anhydrous" means that water is not intentionally added to the composition. A variety of ingredients may be suitable including volatile oils, nonvolatile oils, and mixtures thereof. In the most preferred embodiment of the invention the inorganic pigments are insoluble in the liquid carrier, e.g. they are dispersed rather than solubilized in the liquid carrier.

A. Volatile Liquids

The term "volatile" means that the oil has a measurable vapor pressure, or a vapor pressure of at least 2 mm. of mercury at 20° C. The term "nonvolatile" means that the oil has a vapor pressure of less than 2 mm. of mercury at 20° C. Preferably, the compositions of the invention contain a significant portion of volatile solvents as the liquid carrier. Suitable volatile oils are liquids, and enable easy formulation of the composition of the invention. When the composition of the invention is applied to the desired surface, the volatile solvent of the invention must be capable of flashing off to leave the other ingredients in the composition affixed to the surface. Suitable volatile solvents generally have a viscosity of 0.5 to 10 centipoise at 25° C. Suitable volatile solvents include linear silicones, cyclic silicones, paraffinic hydrocarbons, or mixtures thereof.

1. Volatile Silicones

Cyclic silicones (or cyclomethicones) are of the general formula:

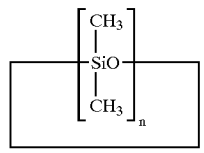

where n=3–6.

Linear volatile silicones in accordance with the invention have the general formula:

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

2. Paraffinic Hydrocarbons

Also suitable as the volatile liquid are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable.

B. Nonvolatile Liquids

The liquid carrier may also comprise low viscosity nonvolatile liquid oils such as silicones, esters, and the like. If the nonvolatile oils are too heavy or greasy it may hamper the long wearing characteristics of the invention. Generally, the viscosity of the nonvolatile oils if present should range from about 11–1000, preferably less than 100 centipoise, most preferably less than about 50 centipoise at 25° C. Examples of such oils include polyalkylsiloxanes, polyarylsiloxanes, and polyethersiloxanes. Examples of such nonvolatile silicones are disclosed in Cosmetics, Science and Technology 27–104 (Balsam and Sagarin ed. 1972); and U.S. Pat. Nos. 4,202,879 and 5,069,897, both of which are hereby incorporated by references. Further non-limiting examples of such silicones include dimethicone, phenyl trimethicone, dimethicone copolyol, and so on.

Also suitable are lower viscosity organic liquids including saturated or unsaturated, substituted or unsubstituted branched or linear or cyclic organic compounds that are liquid under ambient conditions. Preferred organic liquids include those described in U.S. Pat. Nos. 5,505,937; 5,725,845; 5,019,375; and 6,214,329, all of which are incorporated by reference herein in their entirety.

In the preferred composition the liquid carrier comprises one or more nonvolatile liquids either alone or in combination with one or more nonvolatile liquids. Particularly preferred is where the liquid vehicle comprises a mixture of volatile silicone and volatile paraffinic hydrocarbons which serve as the carrier in which the organic pigments are dispersed.

III. Film Film Forming Polymer

The composition preferably comprises 0.1–35%, preferably 0.5–30%, more preferably 1–25% by weight of the total composition of one or more film forming polymers. The film forming polymer (or film former) may be soluble or dispersible in the liquid carrier and when the composition is applied to the desired surface, the liquid carrier at least partially evaporates and causes the film forming polymer to form a film on the surface which holds the organic pigment particles in place with the network created by the hardened polymer. The term "soluble" means that the film forming polymer is soluble in the liquid vehicle and when combined both components form a homogeneous single phase. The term "dispersible" means that the film forming polymer is readily dispersed in the liquid vehicle and forms a stable, heterogeneous composition where the dispersed polymer remains stable and suspended in the liquid vehicle and is compatible therewith (without settling out, for example). The film forming polymer also has adhesive properties, meaning that when incorporated into the claimed composition and applied to the lashes, the film forming polymer forms a film or a weld on the lashes. Such a film will have adhesive and cohesive strength, as is understood by those skilled in the art. Further, the preferred film forming polymer will be capable of forming an semi-permanent film on the surface to which it is applied, meaning that the composition containing the polymer is not removed from the surface to which it is applied with simple soap and water immediately after application.

A variety of film forming polymers may be suitable so long as they are soluble or dispersible in, and compatible with, the liquid carrier; are capable of forming a film on the lashes that may be removed with a remover; and are compatible with the pigment and the liquid carrier. Such polymers may be natural or synthetic and are further described below.

A. Synthetic Polymers

1. Copolymers of Silicone and Ethylenically Unsaturated Monomers

One type of film forming polymer that may be used in the compositions of the invention is obtained by reacting silicone moieties with ethylenically unsaturated monomers. The resulting copolymers may be graft or block copolymers. The term "graft copolymer" is familiar to one of ordinary skill in polymer science and is used herein to describe the copolymers which result by adding or "grafting" polymeric side chain moieties (i.e. "grafts") onto another polymeric moiety referred to as the "backbone". The backbone may have a higher molecular weight than the grafts. Thus, graft copolymers can be described as polymers having pendant polymeric side chains, and which are formed from the "grafting" or incorporation of polymeric side chains onto or into a polymer backbone. The polymer backbone can be a homopolymer or a copolymer. The graft copolymers are derived from a variety of monomer units.

One type of polymer that may be used as the film forming polymer is a vinyl-silicone graft or block copolymer having the formula:

$$\begin{array}{c} (R_1)_{3-x} \quad G_5 \quad (R_3)_{3-q} \\ \diagdown \quad | \quad \diagup \\ Si----(OSi)_y---OSi \\ \diagup \quad | \quad \diagdown \\ (G_2SR_2)_x \quad G_6 \quad (R_4SG_4)_q \end{array}$$

wherein $G_5$ represents monovalent moieties which can independently be the same or different selected from the group consisting of alkyl, aryl, aralkyl, alkoxy, alkylamino, fluoroalkyl, hydrogen, and -ZSA; A represents a vinyl polymeric segment consisting essentially of a polymerized free radically polymerizable monomer, and Z is a divalent linking group such as $C_{1-10}$ alkylene, aralkylene, arylene, and alkoxyalkylene, most preferably Z methylene or propylene.

$G_6$ is a monovalent moiety which can independently be the same or different selected from the group consisting of alkyl, aryl, aralkyl, alkoxy, alkylamino, fluoroalkyl, hydrogen, and -ZSA;

$G_2$ comprises A;

$G_4$ comprises A;

$R_1$ is a monovalent moiety which can independently be the same or different and is selected from the group consisting of alkyl, aryl, aralkyl, alkoxy, alkylamino, fluoroalkyl, hydrogen, and hydroxyl; but preferably $C_{1-4}$ alkyl or hydroxyl, and most preferably methyl.

$R_2$ is independently the same or different and is a divalent linking group such as $C_{1-10}$ alkylene, arylene, aralkylene, and alkoxyalkylene, preferably $C_{1-3}$ alkylene or $C_{7-10}$ aralkylene, and most preferably —$CH_2$— or 1,3-propylene, and $R_3$ is a monovalent moiety which is independently alkyl, aryl, aralkyl, alkoxy, alkylamino, fluoroalkyl, hydrogen, or hydroxyl, preferably $C_{1-4}$ alkyl or hydroxyl, most preferably methyl;

$R_4$ is independently the same or different and is a divalent linking group such as $C_{1-10}$ alkylene, arylene, aralkylene, alkoxyalkylene, but preferably $C_{1-3}$ alkylene and $C_{7-10}$ alkarylene, most preferably —$CH_2$— or 1,3-propylene.

x is an integer of 0–3;

y is an integer of 5 or greater; preferably 10 to 270, and more preferably 40–270; and q is an integer of 0–3.

These polymers are described in U.S. Pat. No. 5,468,477, which is hereby incorporated by reference. Most preferred is poly(dimethylsiloxane)-g-poly(isobutyl methacrylate), which is manufactured by 3-M Company under the tradename VS 70 IBM. This polymer may be purchased in the dry particulate form, or as a solution where the polymer is dissolved in one or more solvents such as isododecane. Preferred is where the polymer is in dry particulate form, and as such it can be dissolved in one or more of the liquids comprising the liquid carrier. This polymer has the CTFA name Polysilicone-6.

Another type of such a polymer comprises a vinyl, methacrylic, or acrylic backbone with pendant siloxane groups and pendant fluorochemical groups. Such polymers preferably comprise comprise repeating A, C, D and optionally B monomers wherein:

A is at least one free radically polymerizable acrylic or methacrylic ester of a 1,1, -dihydroperfluoroalkanol or analog thereof, omega-hydridofluoroalkanols, fluoroalkylsulfonamido alcohols, cyclic fluoroalkyl alcohols, and fluoroether alcohols, B is at least one reinforcing monomer copolymerizable with A, C is a monomer having the general formula X(Y)nSi(R)3-m Z.m wherein X is a vinyl group copolymerizable with the A and B monomers, Y is a divalent linking group which is alkylene, arylene, alkarylene, and aralkylene of 1 to 30 carbon atoms which may incorporate ester, amide, urethane, or urea groups, n is zero or 1;

m is an integer of from 1 to 3,

R is hydrogen, $C_{1-4}$ alkyl, aryl, or alkoxy,

Z is a monovalent siloxane polymeric moiety; and

D is at least one free radically polymerizable acrylate or methacrylate copolymer.

Such polymers and their manufacture are disclosed in U.S. Pat. Nos. 5,209,924 and 4,972,037, which are hereby incorporated by reference. More specifically, the preferred polymer is a combination of A, C, and D monomers wherein A is a polymerizable acrylic or methacrylic ester of a fluoroalkylsulfonamido alcohol, and where D is a methacrylic acid ester of a $C_{1-2}$ straight or branched chain alcohol, and C is as defined above. Most preferred is a polymer having moieties of the general formula: has the general formula:

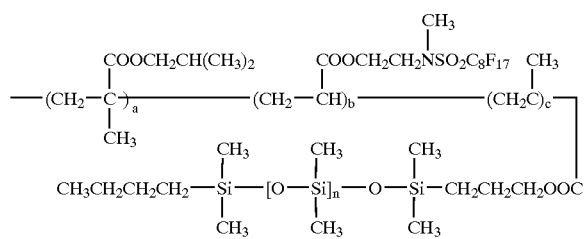

wherein each of a, b, and c has a value in the range of 1–100,000, and the terminal groups are selected from the group consisting of a $C_{1-20}$ straight or branched chain alkyl, aryl, and alkoxy and the like. These polymers may be purchased from Minnesota Mining and Manufacturing Company under the tradenames "Silicone Plus" polymers. Most preferred is poly(isobutyl methacrylate-co-methyl FOSEA)-g-poly(dimethylsiloxane) which is sold under the tradename SA 70-5 IBMMF.

Another suitable silicone acrylate copolymer is a polymer having a vinyl, methacrylic, or acrylic polymeric backbone with pendant siloxane groups. Such polymers as disclosed in U.S. Pat. Nos. 4,693,935, 4,981,903, 4,981,902, and which are hereby incorporated by reference. Preferably, these polymers are comprised of A, C, and optionally B monomers wherein:

A is at least on free radically polymerizable vinyl, methacrylate, or acrylate monomer;

B, when present, is at least one reinforcing monomer copolymerizable with A,

C is a monomer having the general formula:

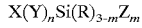

wherein:

X is a vinyl group copolymerizable with the A and B monomers;

Y is a divalent linking group;

n is zero or 1;

m is an integer of from 1 to 3;

R is hydrogen, $C_{1-10}$ alkyl, substituted or unsubstituted phenyl, $C_{1-10}$ alkoxy; and Z is a monovalent siloxane polymeric moiety.

Examples of A monomers are lower to intermediate methacrylic acid esters of $C_{1-12}$ straight or branched chain alcohols, styrene, vinyl esters, vinyl chloride, vinylidene chloride, acryloyl monomers, and so on.

The B monomer, if present, is a polar acrylic or methacrylic monomer having at least one hydroxyl, amino, or ionic group (such as quaternary ammonium, carboxylate salt, sulfonic acid salt, and so on).

The C monomer is as above defined.

Most preferred is where the film forming polymer comprises Polysilicone-6, which is a dry particulate material that may be used as is or solubilized in one or more ingredients that form the liquid carrier.

Examples of other suitable copolymers that may be used herein, and their method of manufacture, are described in detail in U.S. Pat. No. 4,693,935, Mazurek, U.S. Pat. No.4,728,571, and Clemens et al., both of which are incorporated herein by reference. Additional grafted polymers are also disclosed in EPO Application 90307528.1, published as EPO Application 0 408 311, U.S. Pat. No. 5,061,481, Suzuki et al., U.S. Pat. No. 5,106,609, Bolich et al., U.S. Pat. No. 5,100,658, Bolich et al., U.S. Pat. No. 5,100,657, Ansher-Jackson, et al., U.S. Pat. No. 5,104,646, Bolich et al., U.S. Pat. No. 5,618,524, issued Apr. 8, 1997, all of which are incorporated by reference herein in their entirety.

2. Polymers from Ethylenically Unsaturated Monomers

Also suitable for use as film forming polymers are polymers made by polymerizing one or more ethylenically unsaturated monomers. The final polymer may be a homopolymer, copolymer, terpolymer, or graft or block copolymer, and may contain monomeric units such as acrylic acid, methacrylic acid or their simple esters, styrene, ethylenically unsaturated monomer units such as ethylene, propylene, butylene, etc., vinyl monomers such as vinyl chloride, styrene, and so on.

Preferred are polymers containing one or more monomers which are esters of acrylic acid or methacrylic acid, including aliphatic esters of methacrylic acid like those obtained with the esterification of methacrylic acid or acrylic acid with an aliphatic alcohol of 1 to 30, preferably 2 to 20, more preferably 2 to 8 carbon atoms. If desired, the aliphatic alcohol may have one or more hydroxy groups. Also suitable are methacrylic acid or acrylic acid esters esterified with moieties containing alicyclic or bicyclic rings such as cyclohexyl or isobornyl, for example.

The ethylenically unsaturated monomer may be mono-, di-, tri-, or polyfunctional as regards the addition-polymerizable ethylenic bonds. A variety of ethylenically unsaturated monomers are suitable.

Examples of suitable monofunctional ethylenically unsaturated monomers include those of the formula:

I.

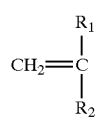

wherein $R_1$ is H, a $C_{1-30}$ straight or branched chain alkyl, aryl, aralkyl; $R_2$ is a pyrrolidone, a $C_{1-30}$ straight or branched chain alkyl, or a substituted or unsubstituted aromatic, alicyclic, or bicyclic ring where the substitutents are $C_{1-30}$ straight or branched chain alkyl, or COOM wherein M is H, a $C_{1-30}$ straight or branched chain alkyl; pyrrolidone, or a substituted or unsubstituted aromatic, alicyclic, or bicyclic ring where the substitutents are $C_{1-30}$ straight or branched chain alkyl which may be substituted with one or more hydroxyl groups, or $[(CH_2)_mO]_nH$ wherein m is 1–20, and n is 1–200.

Preferably, the monofunctional ethylenically unsaturated monomer is of Formula I, above, wherein $R_1$ is H or a $C_{1-30}$ alkyl, and $R_2$ is COOM wherein M is a $C_{1-30}$ straight or branched chain alkyl which may be substituted with one or more hydroxy groups.

More preferably, $R_1$ is H or $CH_3$, and $R_2$ is COOM wherein M is a $C_{1-10}$ straight or branched chain alkyl which may be substituted with one or more hydroxy groups. In the preferred embodiment of the invention, the monofunctional ethylenically unsaturated monomer is a mixture of monomers of Formula I where in one monomer $R_1$ is H or $CH_3$ and $R_2$ is COOM where M is a $C_{1-10}$ alkyl, and where in the second monomer $R_1$ is H or $CH_3$, and $R_2$ is COOM where M is a $C_{1-10}$ alkyl substituted with one or more hydroxy groups.

Di-, tri- and polyfunctional monomers, as well as oligomers, of the above monofunctional monomers may also be used in the composition. Suitable difunctional monomers include those having the general formula:

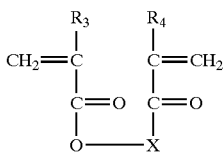

II.

wherein $R_3$ and $R_4$ are each independently H, a $C_{1-30}$ straight or branched chain alkyl, aryl, or aralkyl; and X is $[(CH_2)_xO_y]_z$ wherein x is 1–20, and y is 1–20, and z is 1–100. Particularly preferred are difunctional acrylates and methacrylates, such as the compound of formula II above wherein $R_3$ and $R_4$ are $CH_3$ and X is $[(CH_2)_xO_y]_z$ wherein x is 1–4; and y is 1–6; and z is 1–10.

Particularly preferred are difunctional acrylates and methacrylates, such as the compound of formula II above wherein $R_3$ and $R_4$ are $CH_3$ and X is $[(CH_2)_xO_y]_z$ wherein x is 2; and y is 1, and z is 4. The polymerizable compositions preferably contain 0.1–25%, preferably 0.5–20%, more preferably 1–15% by weight of a difunctional monomer. Particularly preferred is where the difunctional monomer is an ethylene glycol dimethacrylate. Most preferred is where the difunctional monomer is tetraethylene glycol dimethacrylate.

Trifunctional and polyfunctional monomers are also suitable for use in the polymerizable monomer compositions of the invention. Examples of such monomers include acrylates and methacrylates such as trimethylolpropane trimethacrylate or trimethylolpropane triacrylate.

The polymers used in the compositions of the invention can be prepared by conventional free radical polymerization techniques in which the monomer, solvent, and polymerization initiator are charged over a 1–24 hour period of time, preferably 2–8 hours, into a conventional polymerization reactor in which the constituents are heated to about 60–175° C., preferably 80–100° C. The polymers may also be made by emulsion polymerization or suspension polymerization using conventional techniques. Also anionic polymerization or Group Transfer Polymerization (GTP) is another method by which the copolymers used in the invention may be made. GTP is well known in the art and disclosed in U.S. Pat. Nos. 4,414,372; 4,417,034; 4,508,880; 4,524,196; 4,581,428; 4,588,795; 4,598,161; 4,605,716; 4,605,716; 4,622,372; 4,656,233; 4,711,942; 4,681,918; and 4,822,859; all of which are hereby incorporated by reference.

Particularly preferred are polymers of Formula I, above, which are cyclized, in particular, cycloalkylacrylate polymers or copolymers having the following general formulas:

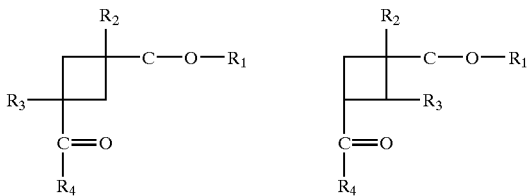

wherein $R_1$, $R_2$, $R_3$, and $R_4$ are as defined above. Typically such polymers are referred to as cycloalkylacrylate polymers. Such polymers are sold by Phoenix Chemical, Inc. under the tradename Giovarez AC-5099M. Giovarez has the chemical name isododecane acrylates copolymer and the polymer is solubilized in isododecane.

3. Silicone Polymers

Also suitable are various types of high molecular weight silicone polymers such as silicone gums, resins, and the like.

Suitable silicone resins include siloxy silicate polymers having the following general formula:

$$[(RR'R'')_3SiO_{1/2}]_x[SiO_2]_y$$

wherein R, R' and R" are each independently a $C_{1-10}$ straight or branched chain alkyl or phenyl, and x and y are such that the ratio of $(RR'R'')_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, which is a blend of about 40–60% volatile silicone and 40–60% trimethylsiloxy silicate. Dow Corning 2-0749 in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41. A similar siloxysilicate resin is available from GE Silicones under the tradename SR1000 and is a fine particulate solid material.

Another type of silicone resin suitable for use in the invention comprises the silicone esters set forth in U.S. Pat. No. 5,725,845 which is hereby incorporated by reference in its entirety. Other polymers that can enhance adhesion to skin include silicone esters comprising units of the general formula $R_aR^E{}_bSiO_{[4-(a+b)/2]}$ or $R^{13}{}_xR^E{}_ySiO_{1/2}$ wherein R and $R^{13}$ are each independently an organic radical such as alkyl, cycloalkyl, or aryl, or, for example, methyl, ethyl, propyl, hexyl, octyl, decyl, aryl, cyclohexyl, and the like, a is a number ranging from 0 to 3, b is a number ranging from 0 to 3, a+b is a number ranging from 1 to 3, x is a number from 0 to 3, y is a number from 0 to 3 and the sum of x+y is 3, and wherein $R^E$ is a carboxylic ester containing radical. Preferred $R_E$ radicals are those wherein the ester group is formed of one or more fatty acid moieities (e.g. of about 2, often about 3 to 10 carbon atoms) and one or more aliphatic alcohol moieities (e.g. of about 10 to 30 carbon atoms). Examples of such acid moieities include those derived from branched-chain fatty acids such as isostearic, or straight chain fatty acids such as behenic. Examples of suitable alcohol moieties include those derived from monohydric or polyhydric alcohols, e.g. normal alkanols such as n-propanol and branched-chain etheralkanols such as (3,3,3-trimethylolpropoxy)propane. Preferably the ester subgroup (i.e. the carbonyloxy radical) will be linked to the silicon atom by a divalent aliphatic chain that is at least 2 or 3 carbon atoms in length, e.g. an alkylene group or a divalent alkyl ether group. Most preferably that chain will be part of the alcohol moiety, not the acid moiety.

Preferably the silicone ester will have a melting point of no higher than about 90° C. It can be a liquid or solid at room temperature. Preferably it will have a waxy feel and a molecular weight of no more than about 100,000 daltons.

Silicone esters having the above formula are disclosed in U.S. Pat. No. 4,725,658 and U.S. Pat. No. 5,334,737, which are hereby incorporated by reference. Preferred silicone esters are the liquid siloxy silicates disclosed in U.S. Pat. No.

5,334,737, e.g. diisostearoyl trimethylolpropane siloxysilicate (prepared in Examples 9 and 14 of this patent), and dilauroyl trimethylolpropane siloxy silicate (prepared in Example 5 of the patent), which are commercially available from General Electric under the tradenames SF 1318 and SF 1312, respectively.

Silicone gums or other types of silicone solids may be used provided they are soluble in the liquid vehicle. Examples of silicone gums include those set forth in U.S. Pat. No. 6,139,823, which is hereby incorporated by reference. Preferred gums have a 600,000 to 1,000,000 centipoise at 25° C.

B. Natural Polymers

Also suitable for use are one or more naturally occuring polymeric materials such as resinous plant extracts including such as rosin, shellac, and the like.

IV. Other Ingredients

A. Plasticizers

It is desirable to incorporate one more plasticizers into the composition. Since the preferred compositions tend to have a lower viscosity when compared to standard mascaras, the plasticizer will improve the spreadability and application of the composition to the surface to which it is applied. The preferred compositions contain one or more plasticizers in an amount sufficient to improve spreadability and application of the composition when compared to the same composition without the plasticizer. Suggested ranges of plasticizers range from about 0.01–20%, preferably about 0.05–15%, more preferably about 0.1–10% by weight of the total composition. A variety of plasticizers are suitable including Suitable plasticizers include glyceryl, glycol, and citrate esters as disclosed in U.S. Pat. No. 5,066,484, which is hereby incorporated by reference. Examples of such esters include glyceryl tribenzoate, glyceryl triacetate, acetyl tributyl citrate, dipropylene glycol dibenzoate, and the like. Also suitable, are plasticizers of the following general formula:

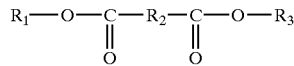

wherein $R_1$, $R_2$, and $R_3$ are each independently a $C_{1-20}$ straight or branched chain alkyl or alkylene which may be substituted with one or more hydroxyl groups. Preferably, $R_1$ is a $C_{3-10}$ straight or branched chain alkyl; $R_2$ is a $C_{2-8}$ alkyl which may be substituted with one or more hydroxyl groups; and $R_3$ is a $C_{3-10}$ straight or branched chain alkyl. Examples of such compounds include dioctyl malate, diisopropyl adipate, dibutyl adipate, dibutyl sebacate, dioctyl azelate, dioctyl succinate, dioctyl fumarate, and the like. Preferred is where $R_1$ and $R_3$ are a branched $C_8$ alkyl, $R_2$ is a $C_2$ alkyl substituted with one hydroxy group, which is dioctyl malate.

Preferred plasticizers are the glycerol, glycol and citrate esters, in particular acetyl tributyl citrate.

B. Viscosity Modifiers

It may also be desirable to include one or more viscosity modifiers in the composition. In particular, since the preferred compositions exhibit a viscosity that is slightly reduced, inclusion of the viscosity modifiers, which will, specifically increase viscosity, cause the composition to have more body and less tendency to run or drip when applied to the desired surface. Suggested ranges of such viscosity modifiers are about 0.01–60%, preferably about 0.05–50%, more preferably about 0.1–45% by weight of the total composition. Preferred are where the viscosity modifiers are not waxes or wax like materials. Suitable viscosity modifiers include natural or synthetic montmorillonite minerals such as hectorite, bentonite, and quaternized derivatives thereof which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like. Particularly preferred is Quaternium-18 hectorite.

Also suitable as the viscosity modifier are various polymeric compounds known in the art as associative thickeners. Suitable associative thickeners generally contain a hydrophilic backbone and hydrophobic side groups. Examples of such thickeners include polyacrylates with hydrophobic side groups, cellulose ethers with hydrophobic side groups, polyurethane thickeners. Examples of hydrophobic side groups are long chain alkyl groups such as dodecyl, hexadecyl, or octadecyl; alkylaryl groups such as octylphenyl or nonyphenyl Another type of viscosity modifier that may be used in the compositions are silicas, silicates, silica silylate, and derivatives thereof. These silicas and silicates are generally found in the particulate form. Particularly preferred is silica.

In the most preferred embodiment of the invention, the compositions are free of wax viscosity modifiers, meaning synthetic and natural waxes such as synthetic wax, castor wax, ceresin, rice wax, and the like, or contain such viscosity modifiers in substantially reduced amounts, generally less than 10% by weight, preferably less than 5% by weight, most preferably less than 1% by weight.

The invention is also directed to a method for improving the wear of cosmetic compositions for making up eyes and skin comprising formulating said products with one or more organic pigments in an amount sufficient to improve the wear of the cosmetic composition.

The wear of the cosmetic composition is improved by including amounts ranging from 0.1–99%, preferably 0.5–85%, more preferably 10–75% by weight of the cosmetic composition of organic pigments. Most unexpectedly, including organic pigments in such compositions greatly increases their wear, meaning that they stay on the surface to which they are applied and provide color for a longer period of time than compositions which do not contain organic pigments. While organic pigments were previously known for providing color, the fact that they are able to increase the wear of a cosmetic composition was not known. In a further preferred embodiment of the claimed method, the wear of the cosmetic composition can be even further improved if the organic pigments are combined with one or more film forming polymers as defined herein. The phrase "improving the wear" means that the composition containing the organic pigments will stay on the skin or hair or lashes longer, e.g. more than one day, and even from one to three days without being removed by soap and water.

The invention will be further described in connection with the following examples which are set forth for the purposes of illustration only.

EXAMPLE 1

A composition for coloring lashes was prepared as follows:

|  | w/w % |
|---|---|
| Dimethicone (1 centipoise) | 20.57 |
| Isododecane | 29.15 |

-continued

| | w/w % |
|---|---|
| Polysilicone-6 | 20.35 |
| Dibutyl adipate | 2.40 |
| Silica | 6.00 |
| Quaternium-18 hectorite/Isododecane/ Propylene carbonate (10/89/1) | 18.00 |
| FD&C Blue #1 Aluminum Lake | 1.44 |
| FD&C Yellow #5 Aluminum Lake | 0.60 |
| D&C Green #5 | 0.05 |
| FD&C Red #40 Aluminum Lake | 1.44 |

The composition was prepared by combining the ingredients and mixing well.

EXAMPLE 2

A composition for coloring lashes was prepared according to the following formula:

| | w/w % |
|---|---|
| Dimethicone (0.65) | 27.09 |
| Isododecane | 6.19 |
| Dioxolane | 4.76 |
| Polysilicone-6 | 17.61 |
| Acetyl tributyl citrate | 2.40 |
| Cyclomethicone/dimethicone/dimethicone vinyl dimethicone crosspolymer | 20.00 |
| Silica | 6.00 |
| Dimethicone copolyol | 3.00 |
| FD&C Blue #1 Aluminum Lake | 1.20 |
| FD&C Yellow #5 Aluminum Lake | 0.50 |
| D&C Green #5 | 0.05 |
| FD&C Red #40 | 1.20 |

The composition was made by combining all of the ingredients and mixing well.

EXAMPLE 3

A composition for coloring lashes was prepared as follows:

| | w/w % |
|---|---|
| Cycloalkylacrylate copolymer in isododecane (50/50) | 50.00 |
| Isopropanol | 6.20 |
| Acetyl tributyl citrate | 1.00 |
| Dimethicone (0.65 centipoise) | 9.00 |
| Dioctyldodecyl fluoroheptyl citrate | 13.00 |
| Fluorocarbon wax | 0.80 |
| Silica silylate | 7.00 |
| Trimethylsiloxysilicate | 10.00 |
| FD&C Blue #1 Aluminum Lake | 1.20 |
| FD&C Yellow #5 Aluminum Lake | 0.50 |
| D&C Green #5 | 0.05 |
| FD&C Red #40 | 1.20 |

The composition was prepared by combining the ingredients and mixing well.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. An anhydrous color cosmetic composition comprising one or more film forming polymers wherein at least one film forming polymer is a silicone resin, said at least one polymer dispersed in a liquid carrier comprising at least one volatile paraffinic hydrocarbon and at least one non-volatile silicone, and organic pigments.

2. The composition of claim 1 wherein the volatile paraffinic hydrocarbon is selected from the group consisting of isododecane, isohexadecane, or mixtures thereof.

3. The composition of claim 1 wherein the non-volatile silicone is selected from the group consisting of dimethicone, phenyl trimethicone, phenyl dimethicone, dimethicone copolyol, alkyl dimethicone copolyol, and mixtures thereof.

4. The composition of claim 1 comprising, by weight of the total composition, about 0.1–25% film forming polymer, and about 0.1–85% liquid carrier, and about 0.05–30% organic pigments or salts thereof.

5. The composition of claim 1 additionally comprising at least one non-volatile ester oil having a viscosity ranging from about 11 to 1,000 centipoise at 25° C.

6. The composition of claim 1 additionally comprising at least one volatile linear silicone.

7. The composition of claim 1 additionally comprising at least one volatile cyclic silicone.

8. The composition of claim 1 additionally comprising inorganic pigments.

9. The composition of claim 1 wherein the inorganic pigments are iron oxides.

10. The composition of claim 1 additionally comprising one or more citrate esters.

11. An anhydrous color cosmetic composition comprising one or more film forming polymers wherein at least one film forming polymer is silicone resin of the formula:

$$[(RR'R'')_3SiO_{1/2}]_x[SiO_2]_y$$

wherein R, R' and R" are each independently a $C_{1-10}$ straight or branched chain alkyl or phenyl, said at least one film forming polymer dispersed in a liquid carrier comprising a volatile paraffinic hydrocarbon selected from the group consisting of isododecane, isohexadecane, and mixtures thereof; at least one non-volatile silicone selected from the group consisting of dimethicone, phenyl trimethicone, phenyl dimethicone, dimethicone copolyol, alkyl dimethicone copolyol and mixtures thereof; and at least one non-volatile ester oil having a viscosity ranging from about 11 to 1,000 centipoise at room temperature, organic pigments and x and y are such that the ratio of $(RR'R'')_3SiO_{1/2}$ units to $SiO_2$ units is 0.5 to 1 to 1.5 to 1.

12. The composition of claim 11 wherein the composition is free of inorganic pigments.

13. The composition of claim 11 which comprises one or more inorganic pigments selected from the group consisting of iron oxides, titanium dioxide, and mixtures thereof.

14. The composition of claim 11 further comprising one or more particulate fillers.

15. The composition of claim 13 wherein the particulate fillers are present ranging from about 0.001–40% by weight of the total composition.

16. The composition of claim 11 further comprising one or more plasticizers which are glyceryl, glycol, or citrate esters or esters of adipic acid.

17. The composition of claim 11 further comprising from about 0.01–60% of one or more viscosity modifiers.

18. The composition of claim 16 wherein the viscosity modifiers comprise synthetic montmorillonite minerals or silica.

19. A colored cosmetic composition comprising a mixture of at least two film forming polymers wherein one is a trimethylsiloxysilicate, and the other is selected from the group consisting of polymers from ethylenically unsaturated monomers, and copolymers of silicone and ethylenically unsaturated monomers; said mixture of at least two film forming polymers dispersed in a carrier comprising at least one volatile solvent selected from the group consisting of paraffinic hydrocarbon, silicone, and mixtures thereof and at least one non-volatile oil selected from the group consisting of silicones, esters, and mixtures thereof; and organic pigments.

20. The composition of claim 18 which is a lipcolor.

21. The composition of claim 18 which is an eyeliner, or lash and brow color.

* * * * *